(12) United States Patent
Aerni

(10) Patent No.: US 9,655,697 B2
(45) Date of Patent: May 23, 2017

(54) UNIVERSAL DIGITAL DENTAL IMPLANT SCANNING CODE AND METHOD

(71) Applicant: William M. Aerni, Strongsville, OH (US)

(72) Inventor: William M. Aerni, Strongsville, OH (US)

(*) Notice: Subject to any disclaimer, the term of this patent is extended or adjusted under 35 U.S.C. 154(b) by 398 days.

(21) Appl. No.: 14/204,543

(22) Filed: Mar. 11, 2014

(65) Prior Publication Data

US 2014/0272790 A1 Sep. 18, 2014

Related U.S. Application Data

(60) Provisional application No. 61/782,525, filed on Mar. 14, 2013.

(51) Int. Cl.
*A61C 8/00* (2006.01)
*A61C 9/00* (2006.01)
*A61B 90/98* (2016.01)

(52) U.S. Cl.
CPC .......... *A61C 8/0093* (2013.01); *A61B 90/98* (2016.02); *A61C 8/0001* (2013.01); *A61C 8/0087* (2013.01); *A61C 9/004* (2013.01); *A61C 8/0022* (2013.01); *A61C 2204/005* (2013.01)

(58) Field of Classification Search
CPC ... A61C 8/0093; A61C 8/0001; A61C 8/0087; A61C 8/004; A61C 8/0022; A61C 2204/005; A61B 90/98
USPC ..................... 433/173, 229, 27, 28
See application file for complete search history.

(56) References Cited

U.S. PATENT DOCUMENTS 6,416,324 B1 * 7/2002 Day ................. A61C 8/008
433/173
2008/0153067 A1 * 6/2008 Berckmans .......... A61C 8/0001
433/213

FOREIGN PATENT DOCUMENTS

WO WO 2011/034781 3/2011

* cited by examiner

*Primary Examiner* — Pedro Philogene
*Assistant Examiner* — David C Comstock
(74) *Attorney, Agent, or Firm* — Fay Sharpe LLP

(57) ABSTRACT

A universal digital implant scanning code (UDDISC) is provided on a dental implant body and/or any device attached to the dental implant body (e.g., the dental implant carrier). Implant bodies and platforms are available in many different types of sizes and configurations from many different companies. The UDDISC allows for an immediate digital scan of the dental implant in relationship to the patient's dentition.

19 Claims, 5 Drawing Sheets

UNIVERSAL DIGITAL DENTAL IMPLANT SCANNING CODE AND METHOD

CROSS REFERENCE TO RELATED PATENTS AND APPLICATIONS

This application claims priority to and the benefit of the filing date of U.S. Provisional Patent Application Ser. No. 61/782,525, filed Mar. 14, 2013, which application is hereby incorporated by reference.

BACKGROUND

The present exemplary embodiment relates generally to dental apparatus and methods. It finds particular application in conjunction with dental implants and methods, and will be described with particular reference thereto. However, it is to be appreciated that the present exemplary embodiment is also amenable to other like applications.

It is common for disease and/or injury to result in the loss of one or more natural teeth throughout a typical person's lifetime. As a result, a number of techniques have been developed to repair and/or replace such lost natural teeth with prosthetics.

In cases where natural teeth remain adjacent to the location where a prosthetic tooth is to be positioned, a fixed bridge may be fabricated. A fixed bridge utilizes one or both adjacent teeth to support the prosthetic tooth. In cases where insufficient natural teeth remain to support and stabilize a bridge, a partial or complete denture may be fabricated, with the denture seating against the patient's gingiva.

In still other cases, a dental implant may be used. A dental implant generally involves making a hole in the upper or lower jaw bone, as appropriate, and then fixing the distal end of the implant in the patient's recipient bone, such as by screwing a threaded implant into the bone. The dental implant is generally sized and positioned so that the proximal end of the implant protrudes at least partially into the space where the prosthetic tooth is to be positioned. Then the prosthetic tooth is fixed to the proximal end of the implant, such that the prosthetic tooth generally occupies the space of the lost tooth.

The current technique for dental implant surgery requires a multi-step process that includes multiple appointments with many procedures to accomplish the final aesthetic implant supported tooth replacement. With reference to FIGS. 1 and 2, in a first appointment an implant body $I_B$ is surgically placed in the dental alveolar bone B in direct relationship to the patient's existing dentition (e.g., between adjacent teeth T). After the implant body $I_B$ is surgically placed, a stock cylinder healing abutment C is placed and secured to the implant body $I_B$.

The non-anatomical stock cylinder healing abutment C causes flattening of the interdental papilla P. The flattening of the interdental papilla P causes dark triangles and gum recession in the smile zone, as seen in FIG. 1. These dark triangles and gum recession are very difficult to correct after the initial healing period.

After four to six months of healing, the patient is seen by the restorative dentist to remove the stock cylinder healing abutment and place an impression post to take a physical impression. This will allow for a physical working model to be made in which a treatment crown can be fabricated at the lab and placed at the next visit. Multiple visits are used to contour the treatment crown in order to reestablish the tissue position (i.e., interdental papilla). This process sometimes involves the restoring dentist to sculpt free hand this anatomy in acrylic or resin material which is extremely time consuming. In addition, this process can have very unpredictable aesthetic results due to the loss of attachment during healing and the varying range of skills of the restoring practitioners.

Today, some dentists use digital scanning and milling machines (CAD-CAM technology) to fabricate onlays, inlays, veneers, etc., on natural teeth with a digitally generated model. These dental restorations can be prepared and placed on the same day (e.g., complete restorations in a single visit). When applying CAD-CAM technology to implant dentistry, a digital model cannot determine the most simple relationship of the implant to the dentition. In particular, conventional scanning techniques cannot determine the implant type (there are approximately 850 types), the diameter and shape of the platform, its orientation and placement location relative to the jawbone, existing teeth and gingiva. These details are essential for a properly designed restoration with a CAD-CAM system because the manner in which the prosthetic tooth mates with the implant impacts the alignment with the adjacent teeth and gingiva.

BRIEF DESCRIPTION

Recent research by Dr. Monish Bhola of Detroit Mercy School of Dentistry, has shown that an anatomically correct crown placed the same day of implant surgery will give the best aesthetic result because the surrounding interdental papilla and gingival tissues will be supported during initial healing. To make an anatomically correct treatment crown on the day of implant surgery is very tedious, time consuming and stressful for the dentist. Presently, the dentist has to work in a sterile surgical site using stock cylinder abutments, acrylic and prefabricated crown forms. The present disclosure merges CAD-CAM technology and same-day surgery placement of an anatomically correct restoration. Aspects of the present disclosure reduce the dentist's time and stress during the fabrication of an anatomically correct restoration at the time of implant surgery. It will also allow for a more consistent end result from practitioner to practitioner. Accordingly, the present disclosure is directed to improved scanning technology for generating anatomically correct prosthetic teeth for same day restorations.

In accordance with one aspect, a universal digital dental implant scanning code (UDDISC) is provided on the implant body and/or any device attached to the dental implant body (e.g., the dental implant carrier). Implant bodies and platforms are available in many different types of sizes and configurations from many different companies. The UDDISC allows for an immediate digital scan of the dental implant in relationship to the patient's dentition. The UDDISC can provide at least the following implant information to the scanning equipment: the implant manufacturer, the platform design type, the platform diameter. This UDDISC can further include one or more orientation mark or marks for communicating the implant's direction/rotation (angular orientation) of the internal or external platform attachment, the implant's platform depth, and/or angle with respect to the jaw bone, teeth and gingiva. This UDDISC can be matched to a data base of codes stored in the digital scanning equipment.

Using the information obtained from the UDDISC, an exact digital rendition of the patient's dentition in relationship to the implant position can be generated so an anatomically correct immediate crown or anatomically correct abutment with cemented crown or an anatomically correct healing abutment, which facilitate in the initial healing of the soft tissue around an implant, can be fabricated and placed the same day as implant surgery or second stage surgery. The same day restorations can include an anatomically correct milled screw retained crown, an anatomically correct milled screw retained abutment with cemented crown, or an anatomically correct milled healing abutment, for example.

The UDDISC associated with any device attached to the dental implant body, or the implant body itself, can be in the form of letters, numbers, shapes, colors or any other type of graphic design as desired. It will be appreciated the each unique UDDISC can be capable of relaying all the identifying markers and other information of the various dental implants for a digital design.

In accordance with another aspect, a dental implant product includes at least a dental implant comprising a first implant portion adapted to be fixed in the bone of a dental patient within the patient's existing dentition, a second implant portion adapted to extend from the bone of a dental patient when the first implant portion is fixed in the bone at the initial surgery of the dental patient, and at least one indicium on the second implant portion that can be scanned on the day of surgical placement of the first implant portion, or second stage surgery, indicative of the conformation of the first implant portion.

The at least one indicium can include a code that is indicative of at least one of the manufacturer, platform design type or platform diameter of the dental implant. The second implant portion can have at least one reference mark indicative of the orientation or position of the dental implant within the bone of the dental patient in relation to the patient's existing dentition. The orientation or position can include at least one of angular position, buccal, lingual, mesial, distal, occlusal, apical and implant angle, in relation to the patient's existing dentition. The first portion can include an embeddable portion of a dental implant body, and the second portion can include a portion of the dental implant body that remains exposed when the first portion is fixed in the bone of a dental patient. The product can further include a sealed sterile vial in which the dental implant is supported.

In accordance with another aspect, a dental implant product including at least a dental implant comprises a first implant portion adapted to be fixed in the bone of a dental patient within the patient's existing dentition, and a second implant portion that can be removed and replaced by a third implant portion having at least one code adapted to be read on the day of initial surgery wherein the first implant portion is fixed, the at least one code indicative of the conformation of the first implant portion within the patient's existing dentition.

The third implant portion can be marked with a code that is indicative of at least one of the manufacturer, platform design type, or platform diameter of the dental implant. The third implant portion can include at least one reference mark indicative of the orientation or position of the dental implant within the bone of the dental patient in relation to the patient's existing dentition. The orientation or position can include at least one of angular position, buccal, lingual, mesial, distal, occlusal, apical and implant angle, in relation to the patient's existing dentition. The implant product can further comprise a sealed sterile vial in which the dental implant is supported.

In accordance with yet another aspect, a method of performing dental restorations comprises the steps of surgically placing a dental implant in the bone of a dental patient within the patient's existing dentition, the dental implant including at least a first implant portion adapted to be fixed in the bone of a dental patient, a second implant portion adapted to extend from the bone of a dental patient when the first implant portion is fixed in the bone of the dental patient, and a code indicative of the conformation of the first implant portion relative to the patient's existing dentition, scanning the patient's dentition and the dental implant with a digital scanner, creating a digital model of the dental implant in relation to the patient's dentition, using the digital model to mill at least one of an anatomically correct screwed retained crown, or an anatomically correct abutment with cemented crown or an anatomically correct healing abutment and seating the milled restoration on the surgically placed dental implant.

All of the recited steps can be performed on the same day of dental implant placement surgery or at second stage surgery to facilitate the support of gum tissue during initial healing in an aesthetic zone. The code can be indicative of at least one of the manufacturer, platform design type, or platform diameter of the dental implant. The dental implant can further include at least one reference mark indicative of the orientation or position of the dental implant within the bone of the dental patient in relation to the patient's existing dentition. The scanning can include scanning the reference marks to determine at least one of angular position, buccal, lingual, mesial, distal, occlusal, apical and implant angle, in relation to the patient's existing dentition. The method can further include fixing the second portion to the first portion after the first portion is surgically placed, wherein the second portion includes the code, and/or scanning the code to obtain at least one characteristic of the implant.

DETAILED DESCRIPTION

Figure 1:
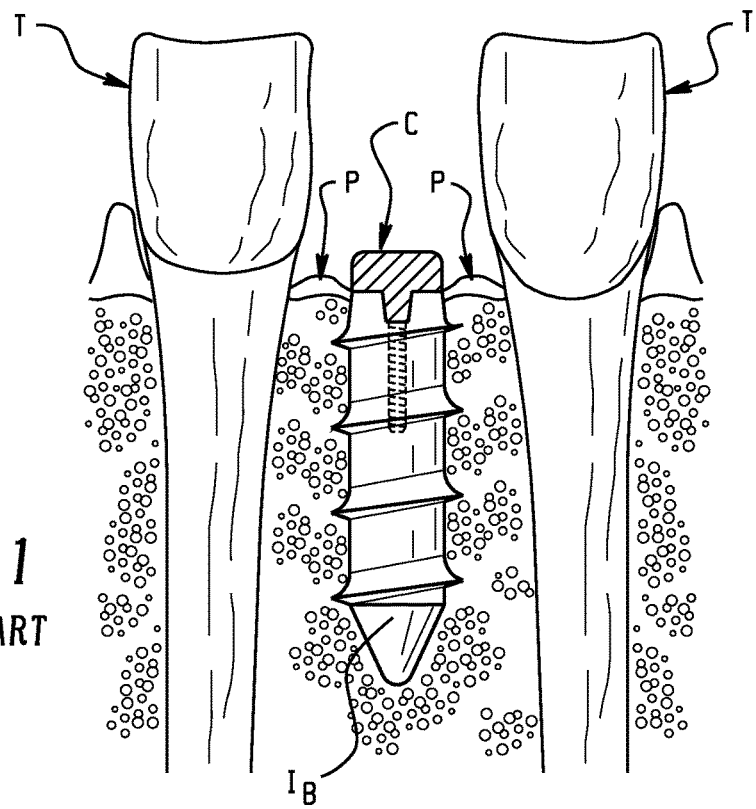
FIG. 1 is a partial cross-sectional view of a prior art dental implant and cylindrical healing abutment.
Figure 2:
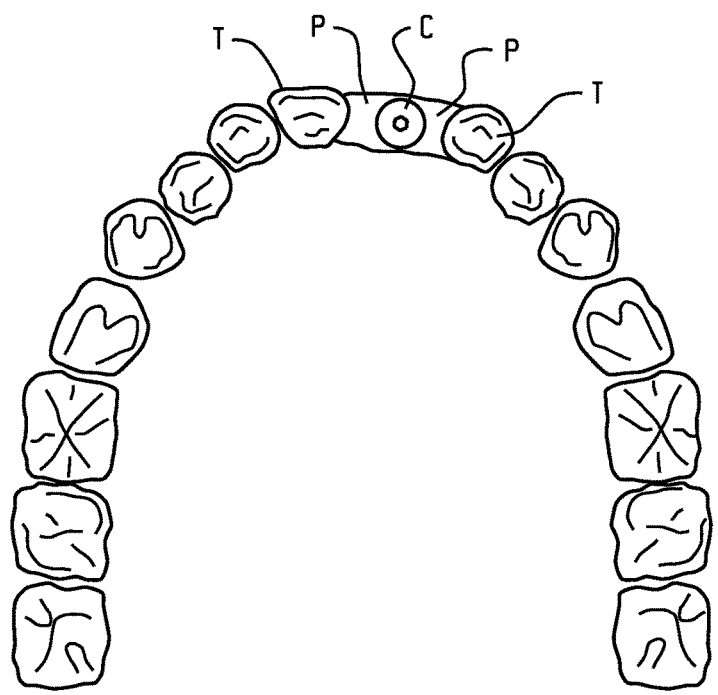
FIG. 2 is a plan view of a patient's dentition including the implant of FIG. 1.
Figure 3:
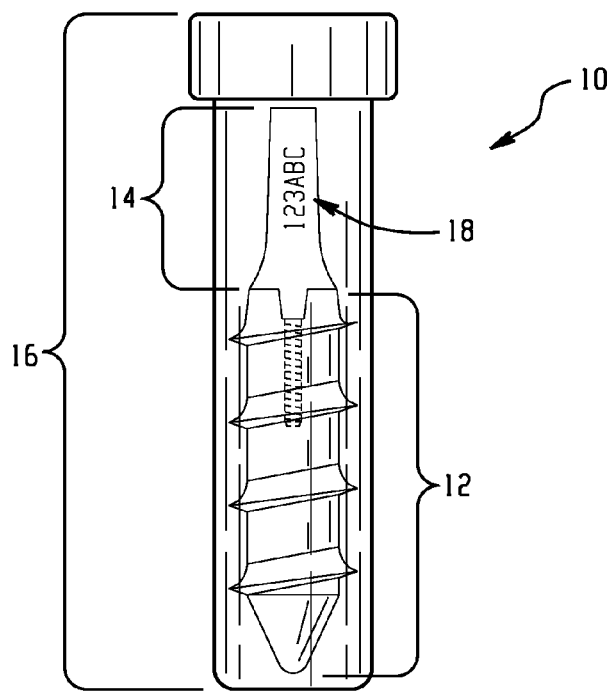
FIG. 3 is a partial cross-sectional view of an exemplary implant product in accordance with the present disclosure.

With reference to FIG. 3, an exemplary sterile dental implant product 10 in accordance with the present disclosure is illustrated. The dental implant product 10 generally includes a dental implant body 12 having external threads or other features for securing the body within a hole in a jaw bone of a patient. An implant carrier 14 is secured to the implant body 12. Both the implant body 12 and the implant carrier 14 are provided within a sterile vial 16. In accordance with the present disclosure, the implant carrier 14 includes a mark, code or other indicium 18. As will be described in more detail below, the indicium can be scanned by an optical (or other) scanning device, and conveys information relating to specific intrinsic and extrinsic characteristic of the implant. The implant body 12 and carrier 14 are exemplary in nature, and it should be appreciated that virtually any design of dental implant can be used in accordance with the present disclosure.

Figure 4:
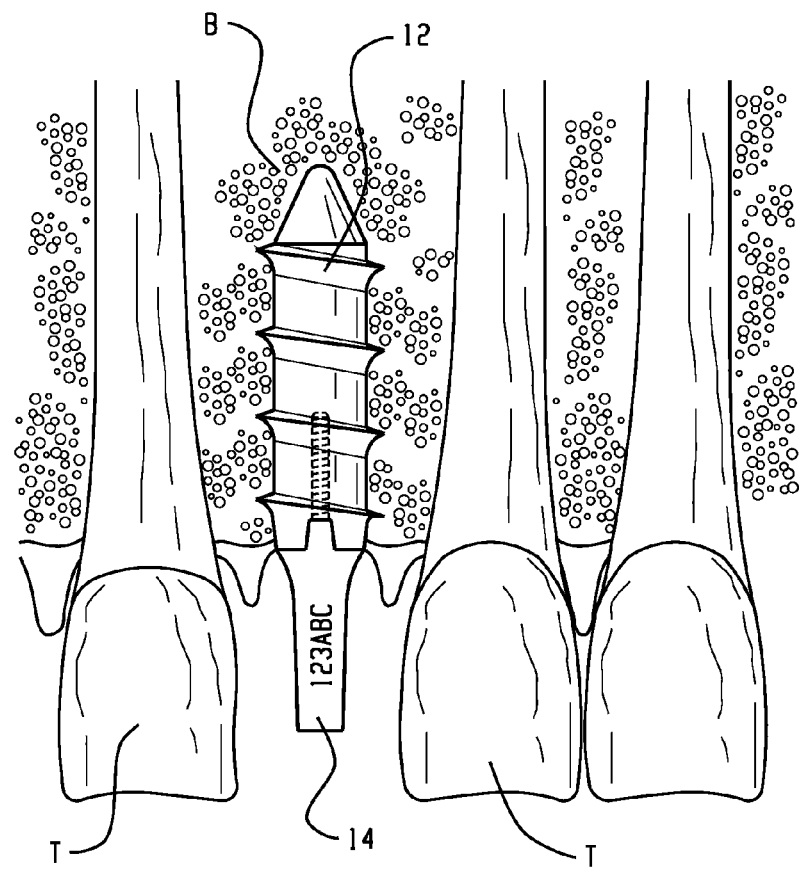
FIG. 4 is a partial cross-sectional view of an implant body and carrier placed on the implant product of FIG. 3 placed in a patient's jaw bone.

Turning to FIG. 4, the implant body 12 is shown after surgical placement in a patient's jaw bone B. Any suitable technique can be used for placing the implant body 12 in accordance with ordinary surgical practices. The carrier 14, after placement of the implant body 12 in the bone B, remains above the surgical site (e.g., above the gumline) such that the indicium 18 can be scanned. That is, once the implant body 12 is placed, the associated carrier 14 remains in a position where the indicium 18 can be scanned by an optical scanner. To this end, the indicium 18 is provided on the side of the carrier 14. It will be appreciated that the indicium 18 could also be provided on any exposed end of the carrier 14, for example.

Once the implant body 12 and carrier 14 are in place, the patient's dentition can be scanned in accordance with known techniques to produce a digital model orienting the implant to the patient's existing dentition which will allow for milling of an anatomically correct crown and/or healing abutment. During the scanning, the indicium 18 on the carrier 14 is read by the scanner, and various intrinsic characteristics of the implant body 12 are obtained such as the implant manufacturer, the platform design type, and the platform diameter, etc. A wide variety of other information regarding the implant can be obtained including implant material type, manufacture date, manufacturer, where it was made, lot number, serial number, expiration date, implant company name, etc.

It will be appreciated that the indicium 18 can be in the form of a unique marking for each different type of implant. In such cases, a scanner can read the unique mark and cross-reference a database of implant characteristics to obtain the specific characteristic of the implant associated with the scanned mark. In this arrangement, the database containing the specific characteristics of the implant can be updated as needed or desired.

In another embodiment, the indicium itself can contain encoded data relating to one or more specific characteristics of the implant with which it is associated. An example of indicium capable of containing such data includes QR codes. In still other embodiments, the implant can be fitted with electronic chips, such as RFID chips or the like, for conveying a unique identifier and/or other information. It will therefore be appreciated that the indicium can include a wide array of markings and/or devices.

In addition to conveying a unique identifier and/or specific data, the indicium can further be used to convey extrinsic information regarding the implant. In this regard, the indicium 18 can further include one or more registration marks that can be scanned to determine the relative position and/or orientation of the implant body 12.

Figure 5A:
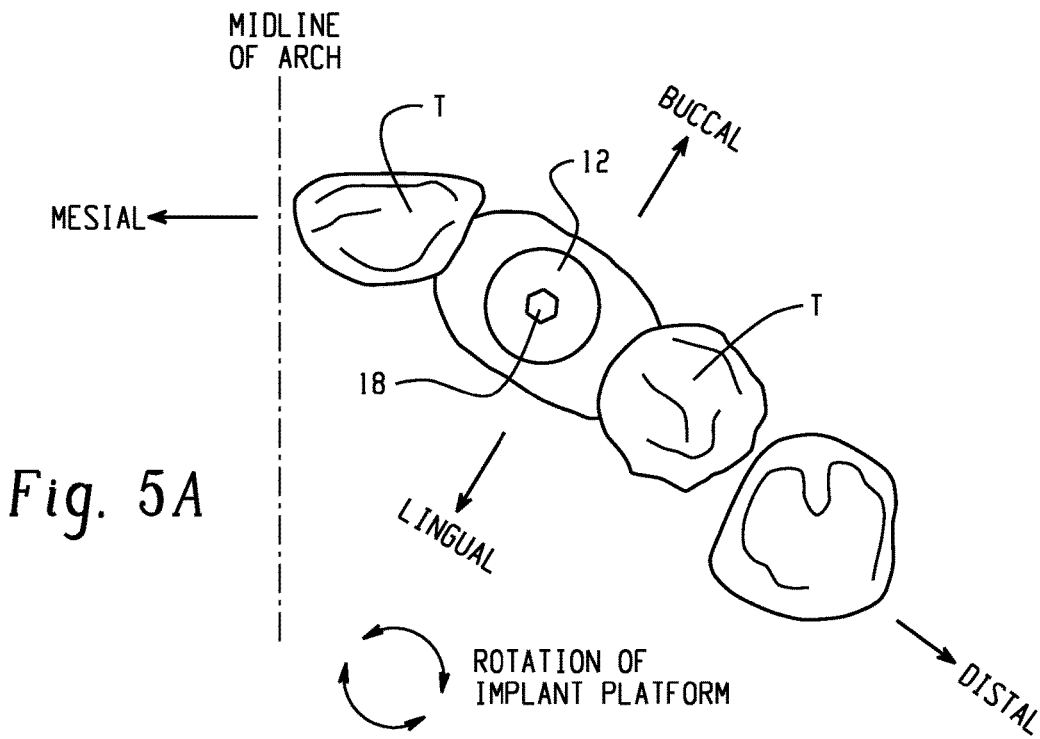
FIG. 5A is a plan view of the patients dentition including the implant body and carrier of FIG. 4.
Figure 5B:
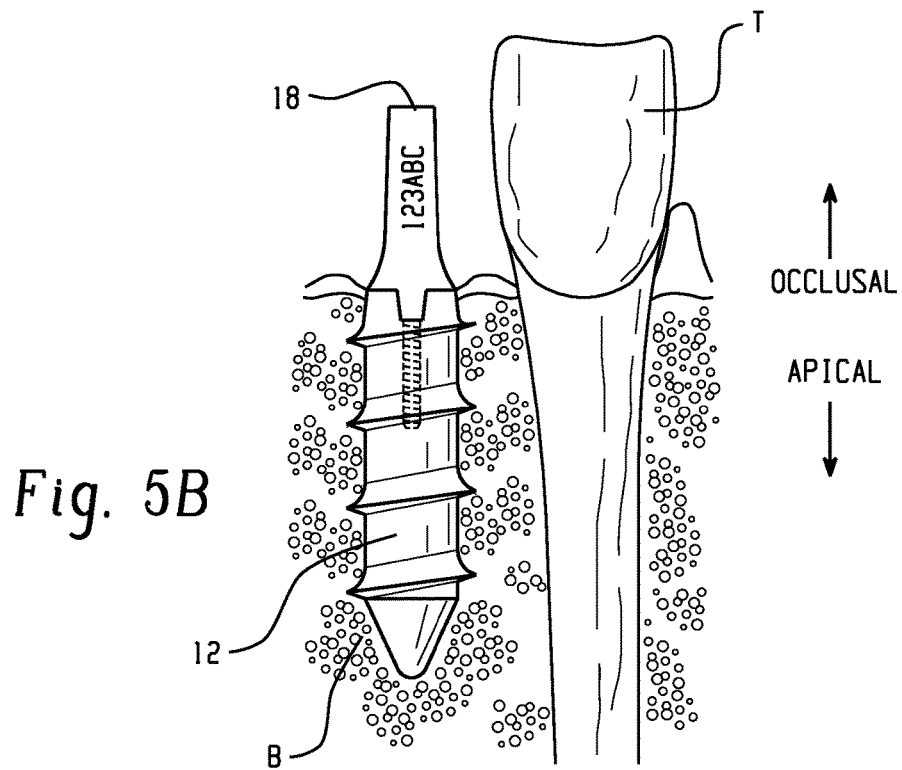
FIG. 5B is a partial cross-sectional view of the implant body and carry of FIG. 4.

Turning to FIGS. 5A and 5B, and initially FIG. 5A, the dental implant 12 and carrier 18 of FIG. 4 are illustrated in plan view, and position descriptions are annotated. The position descriptions include mesial/distal, buccal/lingual, and rotation of the implant about its longitudinal axis. In FIG. 5B, position description apical/occlusal is annotated. These position descriptions are well known in the dental arts.

To assist the scanner in determining the relative location and orientation of the implant, the indicium 18 itself can serve as a reference mark that can be used by the scanner to calculate precise positional information. For example, the indicium 18 can have a particular size and location on the implant body 12 and/or carrier 18. The exact size and location information can be known by the scanner, and can be used to determine the precise location and orientation of the implant after scanning. In another embodiment, separate reference marks can be provided about the length and/or circumference of the implant body 12 and/or carrier 18.

Figure 6:
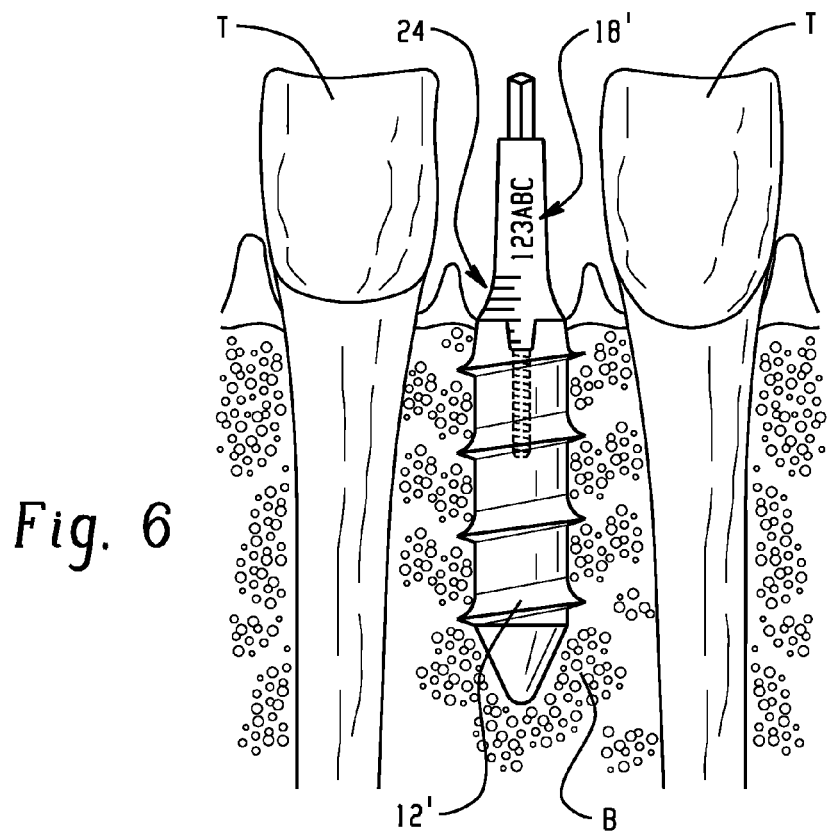
FIG. 6 is a partial cross-sectional view of another exemplary implant body and carrier in accordance with the present disclosure placed in a patient's jaw bone.

For example, in FIG. 6, another exemplary implant body 12' and carrier 18' are illustrated after placement in a patient's jaw bone. The implant carrier 18' includes a plurality of axially spaced apart hash marks 24 that can be scanned by the scanner and used to determine apical/occlusal position of the implant. In the same manner, a plurality of circumferentially spaced registration marks can be provided. Implant angular position can be determined by angle of carrier when scanned because both the implant and carrier will be at the same angle. Implant depth can be determined by the length of the carrier which will be consistent.

Figure 7:
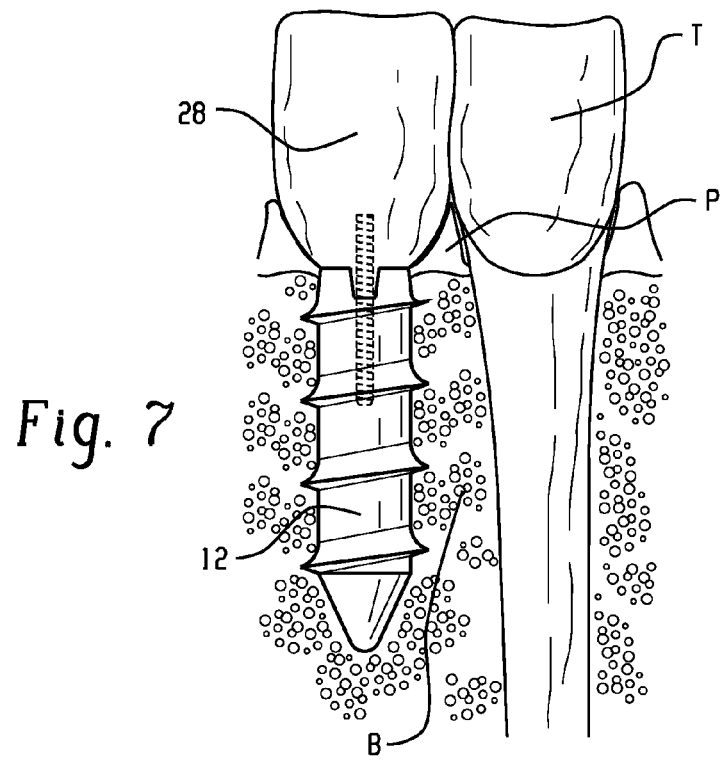
FIG. 7 is a partial cross-sectional view of an exemplary restoration in accordance with the present disclosure.

Turning now to FIG. 7, a restoration in accordance with the present disclosure is shown. The restoration includes an anatomically correct milled screw retained crown 28 mounted to an implant body 12 surgically placed in bone B of a patient's jaw. It will be appreciated that the anatomically correct milled screw retained crown 28 has been made in accordance with present disclosure wherein scanning equipment was used to scan the patient's dentition after placement of the implant body 12. The scanning equipment utilized the UDDISC previously set forth to develop a digital model of the patients dentition, and then the anatomically correct crown was created using CAD-CAM technology and a milling machine (or via other methods) on the same day as placement of the implant body 12. As illustrated, the papilla tissue P is supported by the anatomically correct milled screw retained crown 28.

Figure 8:
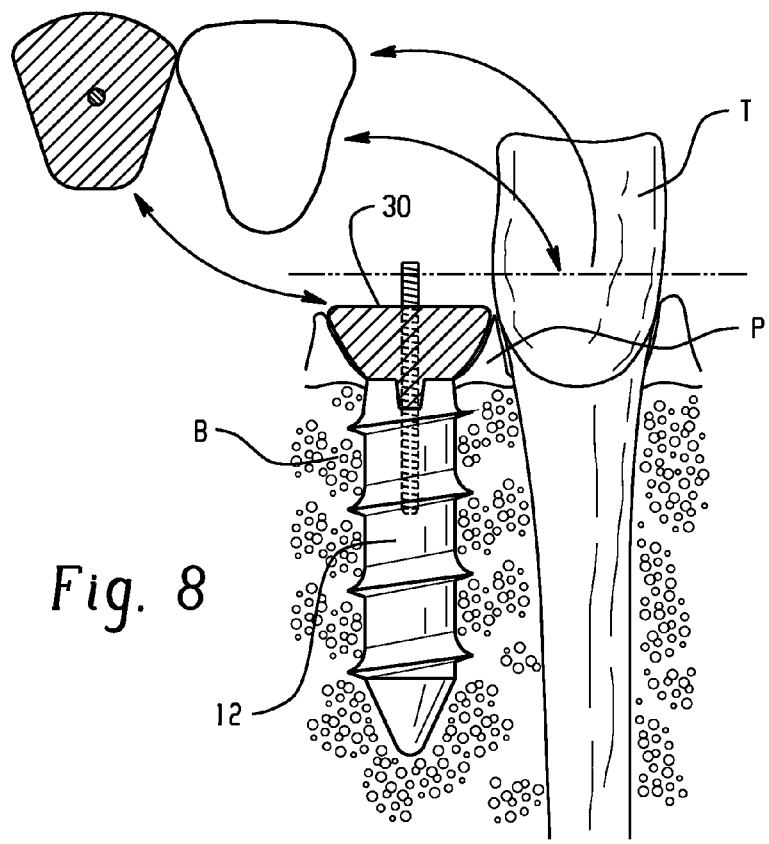
FIG. 8 is a partial cross-sectional view of another exemplary restoration in accordance with the present disclosure.

FIG. 8 shows another restoration in accordance with the present disclosure. In this embodiment, an anatomically correct milled healing abutment 30 is generated and secured to the implant body 12 on the same day as placement of the implant body 12. The healing abutment 30 has been made in accordance with the present disclosure wherein scanning equipment was used to scan the patient's dentition after placement of the implant body 12. The scanning equipment utilized the UDDISC previously set forth to develop a digital model of the patients dentition, and then the anatomically correct healing abutment 30 was created using a CAD-CAM system and a milling machine (or via other methods). In this embodiment, the anatomically correct milled healing abutment 30 is placed the same day as the implant body 12, and then removed at a later date and an anatomically correct crown is fitted to the implant body 12. As illustrated, the papilla tissue P is supported by the anatomically correct healing abutment 30.

Figure 9:
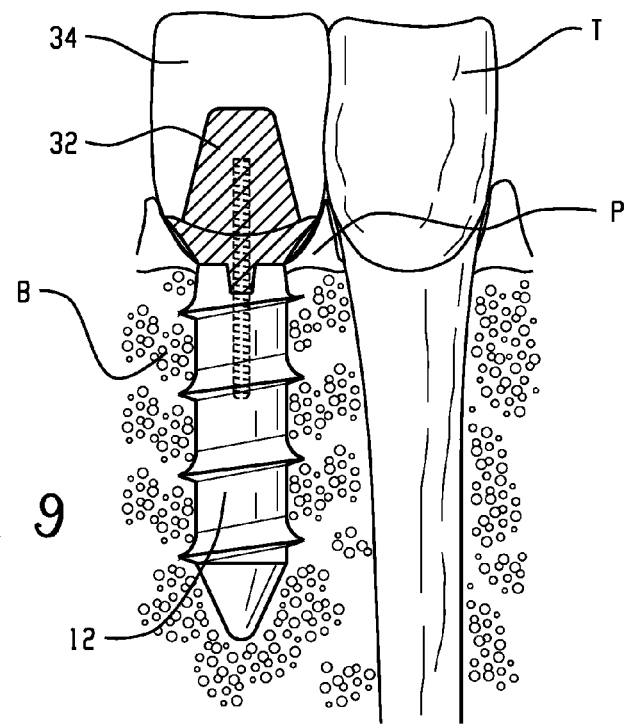
FIG. 9 is a partial cross-sectional view of still another exemplary restoration in accordance with the present disclosure.

FIG. 9 shows yet another restoration in accordance with the present disclosure. In this embodiment, an anatomically correct milled abutment 32 is generated and secured to the implant body 12 on the same day as placement of the implant body 12. The abutment 32 has been made in accordance with the present disclosure wherein scanning equipment was used to scan the patient's dentition after placement of the implant body 12. The scanning equipment utilized the UDDISC previously set forth to develop a digital model of the patients dentition, and then the anatomically correct abutment 30 was created using a CAD-CAM system and a milling machine (or via other methods). In this embodiment, the anatomically correct milled abutment 32 is shaped to receive an anatomically correct crown 34, that can be cemented in place the same day as the placement of the implant body 12. As illustrated, the papilla tissue P is supported by the anatomically correct abutment 32 and cemented crown 34.

As used in this disclosure, the term restoration is intended to encompass a wide variety of dental prosthesis including the above-mentioned anatomically correct milled abutments and crowns. It will be appreciated that a wide range of restorations can be secured to the implant body in a variety of known manners, such as with a screw or cement, without departing from the scope of the present disclosure.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A dental implant product including at least a dental implant comprising a first implant portion adapted to be fixed in the bone of a dental patient within the patient's existing dentition, a second implant portion adapted to extend from the bone of a dental patient when the first implant portion is fixed in the bone at the initial surgery of the dental patient, the second implant portion comprising a carrier removably secured to the first implant portion, and at least one indicium on the second implant portion that can be scanned on the day of surgical placement of the first implant portion, or during a second stage surgery, indicative of the conformation of the first implant portion, and a sealed sterile vial in which the dental implant is supported.

2. The dental implant product of claim 1, wherein the at least one indicium includes a code that is indicative of at least one of the manufacturer, platform design type or platform diameter of the dental implant.

3. The dental implant product of claim 1, wherein the second implant portion has at least one reference mark indicative of the orientation or position of the dental implant within the bone of the dental patient in relation to the patient's existing dentition.

4. The dental implant product of claim 3, wherein the orientation or position includes at least one of angular position, buccal, lingual, mesial, distal, occlusal, apical and implant angle, in relation to the patient's existing dentition.

5. The dental implant product of claim 1, wherein the first portion includes an embeddable portion of a dental implant body, and the second portion includes a portion of the dental implant body that remains exposed when the first portion is fixed in the bone of a dental patient.

6. The dental implant product of claim 1, wherein the first portion includes a dental implant body.

7. The dental implant product of claim 1, wherein the carrier has a first end engaged with the first implant portion and a second end opposite the first end, wherein the second end has a diameter that is smaller than the first end.

8. A dental implant product including at least a dental implant comprising a first implant portion adapted to be fixed in the bone of a dental patient within the patient's existing dentition, and a second implant portion that can be removed and replaced by a third implant portion having at least one code adapted to be read on the day of initial surgery wherein the first implant portion is fixed, the at least one code indicative of the conformation of the first implant portion within the patient's existing dentition, wherein the third implant portion a first end for engaging with the first implant portion and a second end opposite the first end, wherein the second end has a diameter that is smaller than the first end.

9. The dental implant product of claim 8, wherein the third implant portion is marked with a code that is indicative of at least one of the manufacturer, platform design type, or platform diameter of the dental implant.

10. The dental implant product of claim 8, wherein the third implant portion includes at least one reference mark indicative of the orientation or position of the dental implant within the bone of the dental patient in relation to the patient's existing dentition.

11. The dental implant product of claim 10, wherein the orientation or position includes at least one of angular position, buccal, lingual, mesial, distal, occlusal, apical and implant angle, in relation to the patient's existing dentition.

12. The dental implant product of claim 8, further comprising a sealed sterile vial in which the dental implant is supported.

13. A method of performing dental restorations comprising the steps of:
    removing a dental implant from a sterile vial, the dental implant including at least a first implant portion adapted to be fixed in the bone of a dental patient, a second implant portion including a carrier adapted to extend from the bone of a dental patient when the first implant portion is fixed in the bone of the dental patient, and a code indicative of the conformation of the first implant portion relative to the patient's existing dentition;
    surgically placing the dental implant in the bone of a dental patient within the patient's existing dentition,
    scanning the patient's dentition and the code with a digital scanner;
    creating a digital model of the dental implant in relation to the patient's dentition;
    using the digital model to generate a restoration;
    removing the second implant portion from the first implant portion;
    and seating the restoration on the surgically placed first implant portion.

14. The method of claim 13, wherein all of the recited steps are performed on the same day of dental implant placement surgery.

15. The method of claim 13, wherein the code is indicative of at least one of the manufacturer, platform design type, or platform diameter of the dental implant.

16. The method of claim 13, wherein the dental implant further includes at least one reference mark indicative of the orientation or position of the dental implant within the bone of the dental patient in relation to the patient's existing dentition.

17. The method of claim 16, wherein scanning includes scanning the reference marks to determine at least one of angular position, buccal, lingual, mesial, distal, occlusal, apical and implant angle, in relation to the patient's existing dentition.

18. The method of claim 13, further comprising fixing the second portion to the first portion after the first portion is surgically placed, wherein the second portion includes the code.

19. The method of claim 13 further comprising scanning the code to obtain at least one characteristic of the implant.

\* \* \* \* \*